(12) United States Patent
Strom

(10) Patent No.: US 8,871,687 B2
(45) Date of Patent: Oct. 28, 2014

(54) NUCLEIC ACID SEQUENCING BY SINGLE-BASE PRIMER EXTENSION

(75) Inventor: Charles M. Strom, San Clemente, CA (US)

(73) Assignee: Quest Diagnostics Investments Incorporated, Wilmington, DE (US)

(*) Notice: Subject to any disclaimer, the term of this patent is extended or adjusted under 35 U.S.C. 154(b) by 1485 days.

(21) Appl. No.: 12/239,573

(22) Filed: Sep. 26, 2008

(65) Prior Publication Data

US 2009/0088335 A1   Apr. 2, 2009

Related U.S. Application Data

(60) Provisional application No. 60/976,200, filed on Sep. 28, 2007.

(51) Int. Cl.
C40B 30/04   (2006.01)
C12Q 1/68    (2006.01)

(52) U.S. Cl.
CPC .................................. *C12Q 1/6869* (2013.01)
USPC ........................................................... 506/9

(58) Field of Classification Search
None
See application file for complete search history.

(56) References Cited

U.S. PATENT DOCUMENTS

| | | | |
|---|---|---|---|
| 5,736,330 | A | 4/1998 | Fulton |
| 5,760,201 | A | 6/1998 | Glazer et al. |
| 6,046,807 | A | 4/2000 | Chandler |
| 6,057,107 | A | 5/2000 | Fulton |
| 6,268,222 | B1 | 7/2001 | Chandler et al. |
| 6,632,526 | B1 | 10/2003 | Chandler et al. |
| 2002/0015962 | A1 | 2/2002 | Nolan et al. |
| 2006/0177850 | A1 | 8/2006 | Schermer et al. |

OTHER PUBLICATIONS

Kurg et al. (Mar. 2000) Genetic Testing vol. 4 pp. 1 to 7.*
Cai et al. (Jun. 1, 2000) Genomics vol. 66 pp. 135 to 143.*
Braslaysky et al. (Mar. 21, 2003) Proceeding of the National Academy of Sciences USA vol. 100 pp. 3960 to 3964.*
Yang et al. (May 15, 2003) Nucleic Acids Research vol. 31 article e54 pp. 1 to 8.*
Huang et al. (Nov. 2004) Translational Medicine vol. 4 pp. 275 to 279.*
Sphero coated particles (downloaded Sep. 1, 2011 from http://www.spherotech.com/Polystyrene%20Coated%20Particles%20catalog%202010-2011%20rev%20a.pdf) pp. 1 to 7.*
Sphero polystyrene particles (downloaded Sep. 1, 2011 from http://www.spherotech.com/polystyrene%20particles%20catalog%202010-2011%20rev%20a.pdf) pp. 1 to 6.*
Rosenblum et al. (1997) Nucleic Acids Research vol. 25 pp. 4500 to 4504.*
Cal et al., Flow cytometry based minisequencing: A new platform for high-throughput single-nucleotide polymorphism scoring. Genomics 66:135-143, (2000).
Chen et al., A microsphere-based assay for multiplexed single nucleotide polymorphism analysis using single base chain extension. Genome Research 10:549-557, (2000).

(Continued)

*Primary Examiner* — Christian Boesen
(74) *Attorney, Agent, or Firm* — Foley & Lardner LLP

(57) ABSTRACT

The present invention pertains to a method for determining a sequence of contiguous bases within a polynucleotide, the method relying on single-base primer extension using labeled dideoxynucleotide terminators. The primers are immobilized to solid supports (e.g. microspheres or two-dimensional arrays), allowing for the identification of the labeled terminator incorporated into each primer.

21 Claims, 1 Drawing Sheet

(56) References Cited

OTHER PUBLICATIONS

Hafner, et al., Isothermal amplification and multimerization of DNA by Bst DNA polymerase. *Biotechniques* 30:852-6, 858, 860 (2001).
Maniatis et al., *Molecular Cloning, A Laboratory Manual*, 2d, Cold Spring Harbor Laboratory Press, p. 16.54 to 16.55 (1989).
Saiki, "Amplification of Genomic DNA" in *PCR Protocols*, Innis et al., Eds., Academic Press, San Diego, CA, pp. 13-20 (1990).
Wharam, et al., Specific detection of DNA and RNA targets using a novel isothermal nucleic acid amplification assay based on the formation of a three-way junction structure. *Nucleic Acids Res*; 29(11):e54, p. 1-8, (2001).

* cited by examiner

US 8,871,687 B2

NUCLEIC ACID SEQUENCING BY SINGLE-BASE PRIMER EXTENSION

RELATED APPLICATIONS

This application claims priority from U.S. Provisional Application 60/976,200, filed Sep. 28, 2007, incorporated by reference herein in its entirety.

FIELD OF THE INVENTION

The present invention relates generally to the field of nucleic acid sequencing, and more particularly, to methods of nucleic acid sequencing using solid supports.

BACKGROUND OF THE INVENTION

The following description is provided to assist the understanding of the reader. None of the information provided or references cited is admitted to be prior art to the present invention.

Nucleic acid sequencing refers to biochemical methods of determining the order of the nucleotide bases, adenine, guanine, cytosine, and thymine, in an polynucleotide. Determining the nucleic acid sequence is useful in basic research studying fundamental biological processes, as well as in applied fields such as diagnostic or forensic research. The advent of DNA sequencing has significantly accelerated biological research and discovery. The rapid speed of sequencing attainable with modern DNA sequencing technology has been instrumental in the large-scale sequencing of the human genome and DNA sequencing has become increasingly important in molecular diagnostics.

SUMMARY OF THE INVENTION

The present invention pertains to a method for determining a sequence of contiguous bases within a polynucleotide, the method relying on single-base primer extension using labeled dideoxynucleotide terminators. The primers are immobilized to solid supports (e.g. microspheres or two-dimensional arrays), allowing for the identification of the labeled terminator incorporated into each primer. Data on the incorporated terminators is used to determine the base identity of a contiguous sequence of nucleotides in a target nucleic acid.

In one aspect, the present invention provides a method for determining a contiguous sequence comprising at least four bases of a target nucleic acid comprising: (a) preparing one or more reaction mixtures containing the target nucleic acid and four or more primers complementary to a portion of the target nucleic acid such that the primers each have a 3' end located 5' to each nucleotide position of the sequence to be determined, wherein each reaction contains from one to all of said primers in any combination and is under conditions where the primers anneal to the target nucleic acid; (b) extending the one or more primers from step (a) with a polymerase in the presence of one or more labeled dideoxynucleotides; (c) immobilizing said primers to a solid support; and (d) detecting the label of the dideoxynucleotide incorporated into each primer and utilizing this information to determine said contiguous sequence of at least four bases of the target nucleic acid. The primers may extended before immobilization to the solid support, i.e. step (b) occurs before step (c) or extended after immobilization on the solid support, i.e. step (c) occurs before step (a).

In one embodiment, at least two differently-labeled dideoxynucleotides are provided in the same reaction mixture. In another embodiment, four differently-labeled dideoxynucleotides are provided in the same reaction mixture.

In various embodiments, the present invention provides methods for determining a contiguous sequence of four or more bases of a target nucleic acid by performing singleplex single-base primer extension reactions or multiplex single-base primer extension reactions. In one embodiment, the four or more primers corresponding to the entire portion of the target nucleic acid to be sequenced are combined in a single reaction mixture. In another embodiment, two or more primers are combined in one reaction mixture, and two or more primers are combined in an additional reaction mixture or mixtures. Alternatively, the four or more primers are each added to a separate reaction mixture.

In one embodiment, the primers comprise a tag sequence and are immobilized to the solid support via hybridization to a complementary capture oligonucleotide conjugated to the solid support. In another embodiment, the primers are immobilized to the solid support via a covalent attachment.

In one embodiment, the solid support is a labeled microsphere. For example, the microspheres may be made of polystyrene. In one embodiment, the label of each microsphere is optically-detected, based upon varying concentrations of at least two dyes. In certain embodiments, the labeled microspheres and the labeled dideoxynucleotide are detected by flow cytometry.

In another embodiment, the solid support is a two-dimensional array and the immobilized primers are positionally defined on the array. The primers may be immobilized to the array via a covalent attachment or via a linker sequence. In certain embodiments, the extended primers with labeled dideoxynucleotides are detected by scanning the array.

DETAILED DESCRIPTION

Figure 1A:
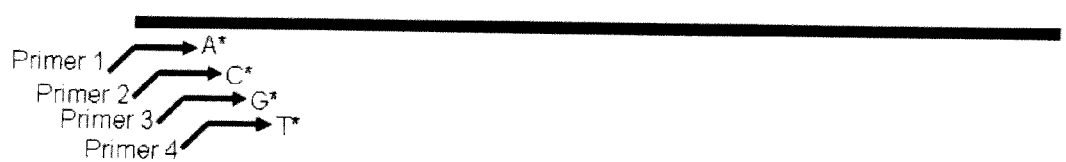
FIG. 1 is a schematic representation of a multiplexed microsphere-based sequencing procedure using tagged primers and capture probe-bearing microspheres.

The present invention relates generally to nucleic acid sequencing methods using solid supports (e.g., microspheres or two-dimensional arrays). The present inventor has discovered that single-base primer extension reactions may be used to determine the base identity of contiguous nucleotides in a target sequence. Accordingly, the methods will determine the contiguous base sequence of target nucleic acids for use in research and molecular diagnostics. The methods are designed to sequence at least 4, at least 5, at least 6, at least 10, at least 20, at least 30, at least 40, at least 50, at least 100, at least 200, or at least 500 contiguous nucleotides.

DEFINITIONS

In the description that follows, a number of terms are utilized extensively. Definitions are herein provided to facilitate understanding of the invention. The terms defined below are more fully defined by reference to the specification as a whole.

Units, prefixes, and symbols may be denoted in their accepted SI form. Unless otherwise indicated, nucleic acids are written left to right in 5' to 3' orientation. Nucleotides may be referred to by their commonly accepted single-letter codes.

The terms "a" and "an" as used herein mean "one or more" unless the singular is expressly specified.

As used herein, "about" means plus or minus 10%.

The terms "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al., Eds., Academic Press, San Diego, Calif., pp 13-20 (1990); Wharam, et al., *Nucleic Acids Res.* 2001 Jun. 1; 29(11):E54-E54; Hafner, et al., *Biotechniques* 30:852-6, 858, 860 (2001); Zhong, et al., *Biotechniques* 30:852-6, 858, 860 (2001).

The term "array" refers to a two-dimensional spatial grouping or an arrangement. In some embodiments, an array refers to a two-dimensional grouping of oligonucleotides (e.g. primers or capture sequences), which serve to interrogate mixtures of target molecules administered to the surface of the array.

The term "capture oligonucleotide" or "capture sequence" refers to an oligonucleotide having a recognition sequence and coupled to a solid surface to hybridize with an oligonucleotide having a "tagging sequence" complementary to the recognition sequence, thereby capturing the target oligonucleotide on the solid surface.

The term "complement," "complementary," or "complementarity" as used herein with reference to polynucleotides (i.e., a sequence of nucleotides such as an oligonucleotide or a target nucleic acid) refers to standard Watson Crick pairing rules. The complement of a nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA. The term "substantially complementary" as used herein means that two sequences specifically hybridize (defined below). The skilled artisan will understand that substantially complementary sequences need not hybridize along their entire length.

As used herein, "nucleic acid," "nucleotide sequence," or "nucleic acid sequence" refer to a nucleotide, oligonucleotide, polynucleotide, or any fragment thereof and to naturally occurring or synthetic molecules. These phrases also refer to DNA or RNA of genomic or synthetic origin which may be single-stranded or double-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose. RNA may be used in the methods described herein and/or may be converted to cDNA by reverse-transcription for use in the methods described herein. Methods for reverse transcription are well known in the art. See, e.g., See Maniatis et al., *Molecular Cloning, A Laboratory Manual*, 2d, Cold Spring Harbor Laboratory Press, page 16-54 (1989).

As used herein, the term "oligonucleotide" refers to a short polymer composed of deoxyribonucleotides, ribonucleotides or any combination thereof. Oligonucleotides are generally between about 10, 11, 12, 13, 14 or 15 to about 150 nucleotides (nt) in length, preferably about 10, 11, 12, 13, 14, or 15 to about 70 nt, and more preferably between about 18 to about 30 nt in length. The single letter code for nucleotides is as described in the U.S. Patent Office Manual of Patent Examining Procedure, section 2422, table 1. In this regard, the nucleotide designation "R" means purine such as guanine or adenine, "Y" means pyrimidine such as cytosine or thymidine (uracil if RNA); and "M" means adenine or cytosine. An oligonucleotide may be used as a primer or as a probe.

As used herein, a "primer" for amplification is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal expression and amplification. The term "primer" as used herein includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of dsDNA. A "reverse primer" is complementary to the sense-strand of dsDNA.

Primers are typically between about 10 and about 100 nucleotides in length, preferably between about 12 and about 30 nucleotides in length, and most preferably between about 15 and about 25 nucleotides in length. There is no standard length for optimal hybridization or polymerase chain reaction amplification. An optimal length for a particular primer application may be readily determined in the manner described in H. Erlich, *PCR Technology, Principles and Application for DNA Amplification* (1989).

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

Equations for calculating $T_m$ and conditions for nucleic acid hybridization are known in the art.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art. As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

Oligonucleotides used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

As used herein, the term "sample" or "test sample" refers to any liquid or solid (or both) material that can be used to test for the presence of nucleic acids. Samples may comprise clinical samples, cells in culture or tissue cells, isolated nucleic acids, or isolated microorganisms. In preferred embodiments, a sample is obtained from a biological source (i.e., a "biological sample"), such as tissue, bodily fluid, or microorganisms collected from a subject. Sample sources include, but are not limited to, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). The term "patient sample" as used herein refers to a sample obtained from a human seeking diagnosis and/or treatment of a disease.

The term "solid support" refers to a material having a rigid or semi-rigid surface or surfaces. In certain embodiments, the solid support will take the form of beads, resins, gels, microspheres, films, matrix layers, silica, or other configurations. In some embodiments, at least one surface of the solid support will be substantially flat.

The terms "target nucleic acid" or "target sequence" as used herein refer to a sequence which includes a segment of nucleotides of interest to be amplified and sequenced. Copies of the target sequence which are generated during the amplification reaction are referred to as amplification products, amplimers, or amplicons. Target nucleic acid may be composed of segments of a chromosome, a complete gene with or without intergenic sequence, segments or portions of a gene with or without intergenic sequence, or sequence of nucleic acids which probes or primers are designed. Target nucleic acids may include a wild-type sequence(s), a mutation, deletion or duplication, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein target nucleic acid may be DNA or RNA extracted from a cell or a nucleic acid copied or amplified therefrom.

As used herein, the term "terminator" or "chain terminating nucleotide" refers to a nucleotide, nucleotide-based nucleotide analog, or acyclo-based analog capable of being added to the terminus of a nucleic acid primer and further capable of specific base-pairing with a nucleotide present in a complementary nucleic acid and which prevents further chain elongation after incorporation at the terminus of a nucleic acid chain. Exemplary terminators include 2',3'-dideoxynucleotides such as ddATP, ddGTP, ddCTP and ddTTP. Analogs of 2',3'-dideoxynucleotide terminators are also included, for example, 5-bromo-dideoxyuridine, 5-methyl-dideoxycytidine and dideoxyinosine are suitable analogs. Other 3'-deoxynucleoside analogs may also be used as terminator nucleotides.

Selection of Targets and Amplification of Nucleic Acids

In one embodiment of the present invention, a target nucleic acid is amplified from a biological sample containing nucleic acids. Nucleic acid samples or isolated nucleic acids may be amplified by various methods known to the skilled artisan. The nucleic acid (DNA or RNA) may be isolated from the sample according to any methods well known to those of skill in the art. If necessary the sample may be collected or concentrated by centrifugation and the like. The cells of the sample may be subjected to lysis, such as by treatments with enzymes, heat surfactants, ultrasonication or combination thereof. The lysis treatment is performed in order to obtain a sufficient amount of DNA from the sample to detect using polymerase chain reaction.

Various methods of DNA extraction are suitable for isolating the DNA. Suitable methods include phenol and chloroform extraction. See Maniatis et al., *Molecular Cloning, A Laboratory Manual,* 2d, Cold Spring Harbor Laboratory Press, page 16-54 (1989). Numerous commercial kits also yield suitable DNA including, but not limited to, QIAamp™ mini blood kit, Agencourt Genfind™, Roche Cobas® or phenol:chloroform extraction using Eppendorf Phase Lock Gels®.

Preferably, PCR is used to amplify nucleic acids of interest. Briefly, in PCR, two primer sequences are prepared that are complementary to regions on opposite complementary strands of the marker sequence. An excess of deoxynucleotide triphosphates (dNTPs) are added to a reaction mixture along with a DNA polymerase, e.g. Taq polymerase. If the target nucleic acid is present in a sample, the primers will bind to the sequence and the polymerase will cause the primers to be extended along the target sequence by adding on nucleotides. By raising and lowering the temperature of the reaction mixture, the extended primers will dissociate from the marker to form reaction products, excess primers will bind to the marker and to the reaction products and the process is repeated, thereby generating amplification products. Cycling parameters can be varied, depending on the length of the amplification products to be extended.

A target nucleic acid can be a polymorphic region of a chromosomal nucleic acid, for example, a gene, or a region of a gene potentially having a mutation. Target nucleic acids include, but are not limited to, nucleotide sequence motifs or patterns specific to a particular disease and causative thereof, and to nucleotide sequences specific as a marker of a disease but not necessarily causative of the disease or condition. For example, target nucleic acids may include disease marker genes (including DNA and mRNA corresponding to the disease marker gene), single nucleotide polymorphisms, and microorganisms (i.e. bacteria and viruses). A target nucleic acid also can be a nucleotide sequence that is of interest for research purposes, but that may not have a direct connection to a disease or that may be associated with a disease or condition, although not yet proven so.

The skilled artisan is capable of designing and preparing primers that are appropriate for amplifying the target nucleic acid in view of this disclosure. Published sequences, including consensus sequences, can be used to design or select primers for use in amplification of template DNA. The selection of sequences to be used for the construction of primers that flank a locus of interest can be made by examination of the sequence of the loci of interest, or immediately thereto. The recently published sequence of the human genome provides a source of useful consensus sequence information from which to design primers to flank a desired human gene locus of interest.

In some embodiments, the methods of the present invention can be applied to sequence any PCR product or other DNA of interest to determine polymorphisms or mutations. One skilled in the art will recognize that numerous applications can be imagined such as presence of histocompatibility alleles associated with susceptibility to diseases, mutations associated with genetic diseases, autoimmune diseases, or mutations of oncogenes or genes associated with neoplasia or risk of neoplasia. In particular, sequence information may be used as a guide to treatment or prevention of various diseases or conditions.

Several genes associated with above named conditions are now known including but not limited to cystic fibrosis gene, multiple endocrine neoplasia type 2a (MEN2a), multiple endocrine neoplasia type 2b (MEN2b), multiple endocrine neoplasia type 1 (MEN 1), ret protooncogene, low density lipoprotein (LDL) receptor, neurofibromatosis type 1 (NF1), neurofibromatosis type 2 (NF2), breast and ovarian cancer susceptibility type 1 (BRCA1), breast and ovarian cancer susceptibility type 2 (BRCA2), breast and ovarian cancer susceptibility type 3 (BRCA3), adenomatous polyposis coli (APC), adenosine deaminase, xeroderma pigmentosum group A correcting gene (XPAC), excision repair cross complementing rodent repair deficiency complementation group 6 (ERCC6), fragile X mental retardation protein 1 (fmr1), Duchenne muscular dystrophy gene, myotonic dystrophy protein kinase, androgen receptor, Huntington's disease associated gene, hypoxanthine-guanine phosphoribotransferase (HPRT), apolipoprotein E, beta-hexosaminidase alpha chain (HEXA), steroid 21-hydroxylase, angiotensin, human nodular mixed lymphocytic and histiocytic cell mismatch repair (hNMLH1 and 2), retinoblastoma susceptibility (Rb), transformation-associated protein 53 (p53), ras, breakpoint cluster region tyrosine-protein kinase (bcr/abl), B-cell leukemia/lymphoma 2 (bcl-2), genes encoding ion transporters, and combination thereof. These genes may or may not be associated with diseases and clinical disorders selected from the group consisting of human myotonia, paramyotonia congenita, hyperkalemic periodic paralysis, hypertrophic cardiomyopathy, hereditary ovalocytic red blood cells, hereditary spherocytosis, glucose/galactose malabsorption, familial hypercholesterolemia, tuberous sclerosis, severe combined immunodeficiency, autoimmune disease, insulin-dependent diabetes mellitus, Cockayne's syndrome, spinal and bulbar muscular atrophy, Peutz-Jegher's syndrome, Lesh-Nyhan syndrome, Tay-Sachs disease, Alzheimers disease, congenital adrenal hyerplasia and hypertension, essential hypertension, hereditary non-polyposis colon cancer, hereditary colon cancer, colon cancer, familial retinoblastoma, Li-Fraumeni syndrome, chronic myelogenous leukemia, follicular and diffuse lymphoma, malignant lymphoma, leukemia, skin cancer, lung cancer, pancreatic cancer, and combinations thereof.

In addition to above named malignancies other types of cancer may comprise fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, rhabdosarcoma, colorectal carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, or mycloma.

In a same way, mutated or wild type (non-mutated) nucleic acid segments from pathogenic organisms, such as bacterial, viral, fungal, mycoplasmal, rickettsial, chlamydial, or protozoan pathogens, are detected simultaneously.

The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well known to the person of ordinary skill in the art. Primers that amplify a nucleic acid molecule can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis or real-time PCR), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 15 to 35 nucleotides in length, preferably 18-25 nucleotides in length.

Single Base Primer Extension (SBE)

General.

In one embodiment, following PCR amplification of the target nucleic acid, the amplicon is denatured and contacted with one or more SBE primers. The primers are bound to solid supports either before or after enzymatic extension (described in further detail below). The primers are designed to anneal to the target nucleic acid immediately 3' of the nucleotide being sequenced or interrogated. Upon hybridization, a polymerase catalyzes a single base primer extension (SBE) reaction. Thus, a SBE reaction includes a primer to be extended, a template which directs the identity of the molecule added to the primer, a polymerase and at least one type of terminator. One or more labeled terminators corresponding to the four nucleoside bases A, C, T, and G are added to the reaction vessel. For example, adding ddNTPs to a polymerization reaction mixture will assure that any extension reaction of the oligonucleotide primer will terminate when the complementary base to the ddNTP in the nucleic acid molecule template is reached.

SBE Primers. SBE primers are single-stranded oligonucleotides comprising a sequence complementary to a target nucleic acid. The length of the SBE primer for use in the present invention depends on several factors including the nucleotide sequence identity and the temperature at which these nucleic acids are hybridized. Typically, the SBE primer may comprise about 10 to 15 nucleotides, about 15 to 20 nucleotides, about 20 to 25 nucleotides, about 25 to 30 nucleotides, or about 30 to 35 nucleotides that are complementary to the target nucleic acid. In suitable embodiments, the SBE primer comprises about 15 to 18 nucleotides that are complementary to the target nucleic acid. The SBE primer may further comprise additional sequences at the 5' end of the primer that are not complementary to the target. In some embodiments, the SBE primer comprises a "tag" sequence complementary to a "capture" sequence conjugated to the solid support (described in further detail below).

Singleplex and Multiplex Sequencing Assays.

At least one primer is provided for each contiguous nucleotide position to be sequenced. In some embodiments, the SBE primers are contacted to the target nucleic acid in a singleplex format, i.e., each SBE primer is provided in a separate reaction vessel. In other embodiments, the SBE primers are contacted to the target nucleic acid in a multiplex format, i.e., in the same reaction vessel. Variations of these embodiments include reactions where some SBE primers for a target nucleic acid are provided in one reaction vessel and other SBE primers are provided in separate reaction vessels. Thus, various embodiments provide for the sequencing of contiguous nucleotides using combinations of SBE primers extended in separate reaction mixtures. The sequence of contiguous nucleotides can be assembled from the separate reactions by (1) determining the identity of the base incorporated into each SBE primer, (2) combining the base identity data from the separate reactions, and (3) arranging the bases by nucleotide position to determine the contiguous sequence sought. Preferably, the sequence assembly is performed by a computer.

Where known polymorphisms exist in the region of complementarity between the SBE primer and the target nucleic acid, it may be necessary to supply multiple primers having a degenerate sequence in order to ascertain the base identity at a specific site. In particular, hybridization of the 3' end of the primer to the target is important in the extension because the elongation occurs at this end. If the sequence at the 3' end of a given primer is variable in the target, then two or more degenerate primers may be supplied in order to determine the sequence of bases 3' of the primer. Where no known polymorphisms exist in the region of complementarity between the SBE primer and the target nucleic acid, only one primer will need to be provided.

In embodiments where the primers are provided in a multiplex format, the design of multiplexed sequencing reactions requires considerations similar to those required for successful multiplex PCR, namely, avoiding primer heterodimers and false priming. Successive primers are designed to overlap in order to sequence contiguous nucleotides in the 5' to 3' direction along the template. Therefore, consideration should be given to competition for binding of primers to adjacent sites. In one embodiment, the length of the primers may be adjusted so that the $T_m$ of overlapping primers is approximately the same. For example, the SBE primers may be designed to have a $T_m$ from about 50° C. to about 70° C., preferably about 60° C. Alternatively, overlapping primers may be provided in separate reaction vessels to minimize competition for binding of primers to adjacent sites.

Terminators.

The primer extension reactions of the present invention can employ one or more labeled terminators. In some embodiments, a SBE reaction is conducted in the presence of a single labeled terminator. In other embodiments, a SBE reaction is conducted in the presence of two or three differently labeled terminators. In suitable embodiments, a SBE reaction is conducted in the presence of four differently-labeled terminators.

A labeled terminator (e.g., ddNTP) may include a detectable label such as a fluorophore. Exemplary fluorophores include e.g., 4-acetamido-4'-isothiocyanatostilbene-2,2'disulfonic acid, acridine and derivatives (acridine, acridine isothiocyanate) Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes), 5-(2'-aminoethyl)aminonaphthalene-1-sulfonic acid (EDANS), 4-amino-N-[3-vinylsulfonyl)phenyl]naphthalimide-3,5 disulfonate (LuciferYellow VS), N-(4-anilino-1-naphthyl)maleimide, anthranilamide, Black Hole Quencher™ (BHQ™) dyes (biosearch Technologies), BODIPY® R-6G, BOPIPY® 530/550, BODIPY® FL, Brilliant Yellow, coumarin and derivatives (coumarin, 7-amino-4-methylcoumarin (AMC, Coumarin 120), 7-amino-4-trifluoromethylcouluarin (Coumarin 151)), Cy2®, Cy3®, Cy3.5®, Cy5®, Cy5.5®, cyanosine, 4',6-diaminidino-2-phenylindole (DAPI), 5',5"-dibromopyrogallol-sulfonephthalcin (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino] naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), Eclipse™ (Epoch Biosciences Inc.), eosin and derivatives (cosin, eosin isothiocyanate), erythrosin and derivatives (erythrosin B, erythrosin isothiocyanate), ethidium, fluorescein and derivatives (5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET)), fluorescamine, IR144, IR1446, Malachite Green isothiocyanate, 4-methylumbelliferone, ortho cresolphthalein, nitrotyrosine, pararosaniline, Phenol Red, B-phycoerythrin, R-phycoerythrin, o-phthaldialdehyde, Oregon Green®, propidium iodide, pyrene and derivatives (pyrene, pyrene butyrate, succinimidyl 1-pyrene butyrate), QSY® 7, QSY® 9, QSY® 21, QSY® 35 (Molecular Probes), Reactive Red 4 (Cibacron® Brilliant Red 3B-A), rhodamine and derivatives (6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, sulforhodamine B, sulforhodamine 101, sulfonyl chloride derivative of sulforhodamine 101 (Texas Red)), N,N,N',N'-tetramethyl-6-carboxyrhodamine (TAMRA), tetramethyl rhodamine, tetramethyl rhodamine isothiocyanate (TRITC), riboflavin, rosolic acid, terbium chelate derivatives.

Solid Supports

In embodiments of the present invention, the sequencing of contiguous nucleotides is carried out, at least in part, using a solid support. A variety of different supports can be used. In some embodiments, the solid support is a single solid support, such as a chip or wafer, or the interior or exterior surface of a tube, cone, or other article. In some embodiments, primers may be immobilized at defined positions on the solid support to generate a two dimensional array. The solid support is fabricated from any suitable material to provide an optimal combination of such desired properties as stability, dimensions, shape, and surface smoothness. Preferred materials do not interfere with nucleic acid hybridization and are not subject to high amounts of non-specific binding of nucleic acids. Suitable materials include biological or nonbiological, organic or inorganic materials. For example, an array can be fabricated from any suitable plastic or polymer, silicon, glass, ceramic, or metal, and can be provided in the form of a solid, resin, gel, rigid film, or flexible membrane. Suitable polymers include, for example, polystyrene, poly(alkyl)methacrylate, poly(vinylbenzophenone), polycarbonate, polyethylene, polypropylene, polyamide, polyvinylidenefluoride, and the like. Preferred materials include polystyrene, glass, and silica. In a particular embodiment, the solid support is a film-based two-dimensional microarray such as the BioFilm-Chip™ available from AutoGenomics (Carlsbad, Calif.).

Dimensions of the solid support are determined based upon such factors as the desired number of regions and the number of sequences to be assayed. As an example, a solid support can be provided with planar dimensions of about 0.5 cm to about 7.5 cm in length, and about 0.5 cm to about 7.5 cm in width. Solid supports can also be singly or multiply positioned on other supports, such as microscope slides (e.g., having dimensions of about 7.5 cm by about 2.5 cm). The dimensions of the solid support can be readily adapted for a particular application.

In some embodiments, the solid support is a particulate support, also referred to as a microsphere, bead or particle. In particular embodiments, the particles are conjugated directly to the SBE primers. In other embodiments, capture oligonucleotides are coupled to particles. Typically, the particles form groups in which particles within each group have a particular characteristic, such as, for example, color, fluorescence frequency, density, size, or shape, which can be used to distinguish or separate those particles from particles of other groups. Preferably, the particles can be separated using techniques, such as, for example, flow cytometry.

The particles can be fabricated from virtually any insoluble or solid material. For example, the particles can be fabricated from silica gel, glass, nylon, resins, Sephadex™ Sepharose™, cellulose, magnetic material, a metal (e.g., steel, gold, silver, aluminum, copper, or an alloy) or metal-coated material, a plastic material (e.g., polyethylene, polypropylene, polyamide, polyester, polyvinylidenefluoride (PVDF)) and the like, and combinations thereof. Examples of suitable micro-beads are described, for example, in U.S. Pat. Nos. 5,736,330, 6,046,807, and 6,057,107, all of which are incorporated herein by reference. Examples of suitable particles are available, for example, from Luminex Corp., Austin, Tex.

In certain embodiments, the support (whether a two-dimensional array or particulate support) is capable of binding or otherwise holding a capture oligonucleotide or SBE primer to the surface of the support in a sufficiently stable manner to accomplish the purposes described herein. Such binding can include, for example, the formation of covalent, ionic, coordinative, hydrogen, or van der Waals bonds between the support and the capture oligonucleotide or SBE primer or attraction to a positively or negatively charged support. Capture oligonucleotides or SBE primers are attached to the solid support surface directly or via linkers. In one embodiment, capture oligonucleotides or SBE primers are directly attached to the support surface by providing or derivatizing either the surface, the oligonucleotide, or both, with one or more reactive groups. In one embodiment, well-known chemical crosslinkers may be used for covalent linkage. For example, amino-labeled primers can be covalently attached to carboxylated solid supports using N-(3-Dimethylaminopropyl)-N'-ethylcarbodiimide hydrochloride (EDAC). In another example, the surface of Luminex™ particles can be modified with, for example, carboxylate, maleimide, or hydrazide functionalities or avidin and glass surfaces can be treated with, for example, silane or aldehyde (to form Schiff base aldehyde-amine couplings with DNA). In some embodiments, the support or a material disposed on the support (as, for example, a coating on the support) includes reactive functional groups that can couple with a reactive functional group on the capture oligonucleotides. As examples, the support can be functionalized (e.g., a metal or polymer surface that is reactively functionalized) or contain functionalities (e.g., a polymer with pending functional groups) to provide sites for coupling the capture oligonucleotides.

As yet another alternative, the support can be partially or completely coated with a binding agent, such as streptavidin, antibody, antigen, enzyme, enzyme cofactor or inhibitor, hormone, or hormone receptor. The binding agent is typically a biological or synthetic molecule that has high affinity for another molecule or macromolecule, through covalent or non-covalent bonding. The SBE primer or capture oligonucleotide is coupled to a complement of the binding agent (e.g., biotin, antigen, antibody, enzyme cofactor or inhibitor, enzyme, hormone receptor, or hormone). The SBE primer or capture oligonucleotide is then brought in contact with the binding agent to hold the capture oligonucleotide on the support. Other known coupling techniques can be readily adapted and used in the systems and methods described herein.

Microspheres. In one embodiment, the present invention utilizes microspheres which are uniquely distinguished by detectable characteristics. The microspheres are alternately termed microparticles, beads, polystyrene beads, microbeads, latex particles, latex beads, fluorescent beads, fluorescent particles, colored particles and colored beads. The microspheres serve as vehicles for molecular reactions. Microspheres for use in flow cytometry may be obtained from manufacturers, such as Luminex Corp. of Austin, Tex. Illustrative microspheres and methods of manufacturing same are, for example, found in U.S. Pat. Nos. 6,268,222 and 6,632,526.

Microspheres may be composed of polystyrene, cellulose, or other appropriate material. In a particular embodiment, microspheres are stained with different amounts of fluorescent dyes. Preferably the dyes have the same or overlapping excitation spectra, but possess distinguishable emission spectra. Fluorescent dyes that may be used in the microspheres include cyanine dyes, with emission wavelengths between 550 nm and 900 nm. These dyes may contain methine groups and their number influences the spectral properties of the dye. The monomethine dyes that are pyridines typically have blue to blue-green fluorescence emission, while quinolines have green to yellow-green fluorescence emission. The trimethine dye analogs are substantially shifted toward red wavelengths, and the pentamethine dyes are shifted even further, often exhibiting infrared fluorescence emission (see for example U.S. Pat. No. 5,760,201). However, any dye that is soluble in an organic solvent can be used.

The classification parameters of each microsphere advantageously includes one, two, three, four, or more standard fluorochromes or fluorescent dyes. The one or more fluorochromes are affixed to or embedded in each microsphere by any standard method, for example, by attachment to the microsphere surface by covalent bonding or adsorption. Alternatively, the dye(s) may be affixed by a copolymerization process, wherein monomers, such as an unsaturated aldehyde or acrylate, are allowed to polymerize in the presence of a fluorescent dye, such as fluoroscein isothiocynate (FITC), in the resulting reaction mixture.

Another method by which one or more dyes are embedded in a microsphere includes adding a subset of microspheres to, for example, an organic solvent to expand the microspheres. An oil-soluble or hydrophobic dye, for example, is subsequently added to the subset of microspheres, thereby penetrating into each microsphere. After incubating the resulting combination, an alcohol or water-based solution, for example, is added to the combination and the organic solvent is removed. The microsphere shrinks, retaining the dye(s) inside. Each fluorochrome in the microsphere optionally serves as an additional or alternative classification parameter.

Each of the microspheres are addressed to a unique primer or linker sequence, allowing the analysis of many nucleotide positions in a single reaction. After a single base primer extension reaction, the particles are supplied to a reader system, which determines the particle IDs to identify the particle types and also detects the reporter signals. The reader system includes multiple excitation light sources, such as laser or other devices with controlled wavelengths and optical power, such as LEDs, SLDs, broadband sources with excitation filters, and so forth. The light sources excite the various reporters to supply associated signals to one or more detectors. Emission filters and wavelength discriminators are included such that a given detector receives at a given time the signals associated with a single assay binding label.

Capture and Tag Oligonucleotides

In one embodiment, the SBE primers are indirectly immobilized to a solid support (e.g. microsphere or two-dimensional array) via a linker sequence. In this embodiment, each SBE primer may have a unique nucleic acid 5' tag sequence, which is complementary to a capture oligonucleotide conjugated to the solid support (e.g., microsphere or two-dimensional array). Thus, the capture oligonucleotide includes a recognition sequence that can capture, by hybridization, a target oligonucleotide having a complementary tagging sequence. The hybridization of the recognition sequence of a capture oligonucleotide and the tagging sequence of a target oligonucleotide results in the coupling of the target oligonucleotide to the solid support. The recognition sequence and tagging sequence are associated with a particular SBE primer sequence (also part of the target nucleic acid).

The coding and tagging sequences typically include at least six nucleotides and, in some instances, include at least 8, 10, 15, or 20 or more nucleotides. The capture oligonucleotide also typically includes a functional group that permits binding of the capture oligonucleotide to the solid support or functional groups disposed on or extending from the solid support. The functional group can be attached directly to the polymeric backbone or can be attached to a base in the nucleotidic sequence. As an alternative, the capture oligonucleotide can include a crosslinking portion to facilitate crosslinking, as described above, or can be electrostatically held on the surface. The capture oligonucleotides can be formed by a variety of techniques, including, for example, solid state synthesis, DNA replication, reverse transcription, restriction digest, run-off transcription, and the like. Commercial capture and linker sequence sets are provided by TagIt™ (Luminex, Austin, Tex.) and ZipCode™ (Celera, Rockville, Md.)

In one embodiment, solid supports with associated capture oligonucleotides are disposed in a holder, such as, for example, a vial, tube, or well. After a primer extension reaction, the SBE primers are added to the holder under hybridization conditions. The groups of supports are then investigated to determine which support(s) have attached target oligonucleotides. Optionally, the supports can be washed to reduce the effects of cross-hybridization. One or more washes can be performed at the same or different levels of stringency, as described below. As another optional alternative, prior to contact with the support(s) and capture oligonucleotides, the solution containing target oligonucleotides can be subjected to, for example, size exclusion chromatography, differential precipitation, spin columns, or filter columns to remove primers that have not been amplified or to remove other materials that are not the same size as the target oligonucleotides.

Sequence Determination by Flow Cytometry

General. In one embodiment, flow cytometry is used to analyze the reaction product of the single base primer extension reaction. Flow cytometry is capable of sensitive and quantitative fluorescence measurements of individual particles without the need to separate free from particle-bound label. Analysis rates are very high (hundreds to thousands of particles per second), and multiple fluorescence and light scatter signals can be detected simultaneously.

In some embodiments, the methods utilize encoded particles having a particular detectable signature that are conjugated to a specific primer, or in the case of a sandwich assay, with a capture oligonucleotide, to form particle types. The sets of particle types are then pooled, and aliquots of the particle types are removed to assay vessels. Samples with at least one or more labeled reporter molecules (one for each nucleotide base A, C, T, and G) are supplied to the respective vessels. Following primer extension, the encoded particles and reporter molecules can be detected using a flow cytometer that is capable of reading the molecule to determine both the identity of the microsphere and of the labeled terminator. Alternatively, primer extension may occur prior to contacting the primers with the encoded particles. A computer may be used to associate the particle ID signature and the reporter molecule with a specific nucleotide base at a particular position.

For each microsphere/SBE product supplied, the reader system determines the particle ID and the identity of the reporter (terminator label). Each particle ID is associated with a SBE primer designed to interrogate a specific nucleotide position. Using this information, together with data on which label is incorporated into the SBE product, the nucleotide base identity can be determined for a specific position on an oligonucleotide template.

Typically, one primer is used per nucleotide to be sequenced. These primers may be provided together in a multiplex reaction, or in separate reaction vessels. Where the region of the target corresponding to the primer contains known polymorphisms (particularly at the 3' end of the primer), multiple primers may be used to account for the variability. This ensures that at least one primer in the mixture is complementary to the target, allowing for primer extension. Where the region of the target corresponding to the primer contains unknown polymorphisms, the SBE primer may fail to anneal to the template and/or provide a 3' hydroxyl for primer extension. Consequently, no primer extension will occur (or it may occur at reduced levels). If there is no detectable terminator incorporation, then the system will read that position as a deletion. A microsphere that produces no primer extension or label incorporation suggests that the SBE primer failed to appropriately anneal to the target. Such a result may be indicative of an previously unknown sequence polymorphism within the region of the primer.

Sequence Determination Using Two-Dimensional Array Scanning

In one embodiment of the invention, the solid support is a two-dimensional microarray or biochip. The SBE primers are immobilized on the array at predetermined positions either before or after primer extension. In embodiments where the primers are conjugated directly to the array, the primers are extended on the array. In embodiments where the primers are immobilized via a linker sequence, the primers are extended before, after, or during hybridization to the array. Following primer extension, the fluorescent label from the dideoxynucleotide can be detected at a particular position on the array by scanning the fluorescence at each position, thereby allowing for the determination of the sequence at that location.

In one embodiment, the microarray of the present invention comprises a film-based microarray such as the BioFilm-Chip™ available from AutoGenomics (Carlsbad, Calif.). These biochips comprise a matrix layer coupled to a substrate, wherein the matrix layer includes a plurality of oligonucleotides in a plurality of predetermined positions. The term "predetermined position" of an analyte refers to a particular position of the analyte on the chip that is addressable by at least two coordinates relative to a registration marker on the chip, and particularly excludes a substantially complete coating of the chip with the analyte and/or probe. Therefore, preferred pluralities of predetermined positions will include an array with a multiple rows of substrates forming multiple columns.

In some embodiments, matrix layers may be multi-functional matrix layers that reduce autofluorescence, incident-light-absorption, charge-effects, and/or surface unevenness of the substrate, and contemplated biochips may comprise additional matrix layers. This microarray may be used with a platform such as the Infiniti™ Analyzer, also available from AutoGenomics (Carlsbad, Calif.). Other suitable approaches include the microarray technology commercially available from a variety of sources.

For each address on the array, the reader system determines the identity of the reporter, i.e. terminator label. Each address is associated with a SBE primer designed to interrogate a specific nucleotide position. Using this information, together with data on which label is incorporated into the SBE product, the nucleotide base identity can be determined for a specific position on an oligonucleotide template.

All publications, patent applications, issued patents, and other documents referred to in the present disclosure are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

EXAMPLES

The present invention is further illustrated by the following examples, which should not be construed as limiting in any way.

Example 1

Nucleic Acid Sequencing by Flow Cytometry

In accordance with the present invention, the methods can be applied to sequence any PCR product or other DNA of interest to determine polymorphisms or mutations. Nucleic acids used for this assay may include an amplified nucleic acid from a specimen, e.g., blood cell or pathogen obtained as a result of polymerase chain reaction (PCR).

FIG. 1A is a schematic representation of a multiplexed microsphere-based sequencing procedure using soluble sequence-tagged primers and capture probe-bearing microspheres. For illustrative purposes, the base identity of four contiguous nucleotides is shown. The sample DNA template is amplified by PCR, and the resulting product treated to remove unconsumed dNTPs and PCR primers.

The SBE primer, designed to interrogate a specific site on the template DNA, and bearing a 5'-sequence tag is prepared for each contiguous nucleotide to be sequenced. The tagged primer is added to the template DNA (1 µL, 1 nM), DNA polymerase (1 U, Thermosequenase, Amersham, Piscataway, N.J.), 5 µM of each fluorescein-labeled ddNTP, and buffer (Thermosequenase buffer, Amersham) in a total volume of 10 µL. The reaction mixtures are cycled 99 times at 94° C. for 10 s and 60° C. for 10 s in a thermal cycler.

Figure 1B:
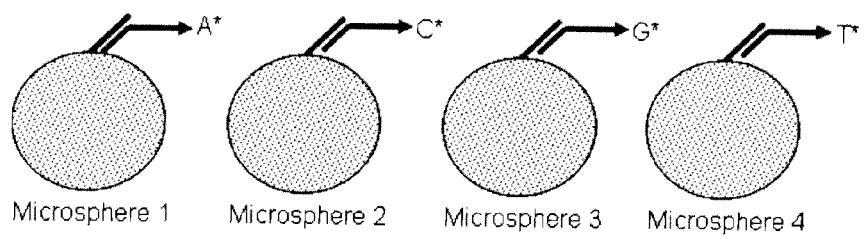

FIG. 1B illustrates the microspheres and the captured extended primers to be analyzed using flow cytometry. Five microliters of microspheres are added to the reaction mixture to capture the biotinylated primers. Two microliters of each reaction mixture is diluted into 500 µL of TEB buffer (50 mM Tris-HCl, pH, 8.0, 0.5 mM EDTA, 0.5% (w/v) bovine serum albumin, BSA), and the microsphere-associated fluorescence is measured using flow cytometry.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method for determining a contiguous sequence comprising at least four bases of a target nucleic acid comprising:
   (a) preparing one or more reaction mixtures containing the target nucleic acid and four or more different, overlapping primers, each primer being complementary to a portion of the target nucleic acid such that the primers each have a 3' end that hybridizes immediately 3' of a different nucleotide position of the contiguous sequence to be determined, wherein each reaction contains from one to all of said primers in any combination and is under conditions where the primers anneal to the target nucleic acid;

(b) extending the one or more primers from (a) with a polymerase in the presence of one or more different dideoxynucleotides, each type of dideoxynucleotide having a different label;

(c) immobilizing said one to all of primers to a solid support; and (d) detecting the label of the dideoxynucleotide incorporated into each primer and utilizing this information to determine said contiguous sequence of at least four bases of the target nucleic acid, wherein immobilizing in (c) occurs before preparing in (a).

2. The method of claim 1, wherein at least two differently-labeled dideoxynucleotides are provided in the same reaction mixture.

3. The method of claim 1, wherein four differently-labeled dideoxynucleotides are provided in the same reaction mixture.

4. A method for determining a contiguous sequence comprising at least four bases of a target nucleic acid comprising:

(a) preparing one or more reaction mixtures containing the target nucleic acid and four or more different, overlapping primers, each primer being complementary to a portion of the target nucleic acid such that the primers each have a 3 end that hybridizes immediately 3' of a different nucleotide position of the contiguous sequence to be determined, wherein each reaction contains from one to all of said primers in any combination and is under conditions where the primers anneal to the target nucleic acid;

(b) extending the one or more primers from (a) with a polymerase in the presence of one or more different dideoxynucleotides, each type of dideoxynucleotide having a different label;

(c) immobilizing said one to all of primers to a solid support; and (d) detecting the label of the dideoxynucleotide incorporated into each primer and utilizing this information to determine said contiguous sequence of at least four bases of the target nucleic acid;

wherein the four or more primers are added to separate reaction mixtures.

5. The method of claim 1, wherein the four or more primers are added to the same reaction mixture.

6. The method of claim 5, wherein four differently-labeled dideoxynucleotides are provided in the same reaction mixture.

7. The method of claim 1, wherein the primers comprise a tag sequence and are immobilized to the solid support via hybridization to a complementary capture oligonucleotide conjugated to the solid support.

8. A method for determining a contiguous sequence comprising at least four bases of a target nucleic acid comprising:

(a) preparing one or more reaction mixtures containing the target nucleic acid and four or more different, overlapping primers, each primer being complementary to a portion of the target nucleic acid such that the primers each have a 3' end that hybridizes immediately 3' of a different nucleotide position of the contiguous sequence to be determined, wherein each reaction contains from one to all of said primers in any combination and is under conditions where the primers anneal to the target nucleic acid;

(b) extending the one or more primers from (a) with a polymerase in the presence of one or more different dideoxynucleotides, each type of dideoxynucleotide having a different label;

(c) immobilizing said one to all of primers to a solid support; and (d) detecting the label of the dideoxynucleotide incorporated into each primer and utilizing this information to determine said contiguous sequence of at least four bases of the target nucleic acid;

wherein the primers are immobilized to the solid support via a covalent attachment.

9. A method for determining a contiguous sequence comprising at least four bases of a target nucleic acid comprising:

(a) preparing one or more reaction mixtures containing the target nucleic acid and four or more different, overlapping primers, each primer being complementary to a portion of the target nucleic acid such that the primers each have a 3' end that hybridizes immediately 3' of a different nucleotide position of the contiguous sequence to be determined, wherein each reaction contains from one to all of said primers in any combination and is under conditions where the primers anneal to the target nucleic acid;

(b) extending the one or more primers from (a) with a polymerase in the presence of one or more different dideoxynucleotides, each type of dideoxynucleotide having a different label;

(c) immobilizing said one to all of primers to a solid support; and (d) detecting the label of the dideoxynucleotide incorporated into each primer and utilizing this information to determine said contiguous sequence of at least four bases of the target nucleic acid;

wherein the solid support is a labeled microsphere.

10. The method recited in claim 9, wherein the microspheres are polystyrene.

11. The method of claim 9, wherein the primers are immobilized to the microspheres via a covalent attachment.

12. The method recited in claim 9, wherein the label of each microsphere is optically-detected, based upon varying concentrations of at least two dyes.

13. The method of claim 12, wherein the microspheres and labeled dideoxynucleotide are detected by flow cytometry.

14. The method of claim 1, wherein the solid support is a two-dimensional array and the immobilized primers are positionally defined on the array.

15. The method of claim 14, wherein the labeled dideoxynucleotides are detected by scanning the array.

16. The method of claim 14, wherein the primers are immobilized to the array via a covalent attachment.

17. A method for determining a contiguous sequence comprising at least four bases of a target nucleic acid comprising:

(a) preparing one or more reaction mixtures containing the target nucleic acid and four or more different, overlapping primers, each primer being complementary to a portion of the target nucleic acid such that the primers each have a 3' end that hybridizes immediately 3' of a different nucleotide position of the contiguous sequence to be determined, wherein each reaction contains all of said primers and is under conditions where the primers anneal to the target nucleic acid;

(b) extending the four or more primers from (a) with a polymerase in the presence of four or more different dideoxynucleotides, each type of dideoxynucleotide having a different label;
(c) immobilizing said primers to a solid support; and
(d) detecting the label of the dideoxynucleotide incorporated into each primer and utilizing this information to determine said contiguous sequence of at least four bases of the target nucleic acid wherein immobilizing in (c) occurs before preparing in (a).

18. A method for determining a contiguous sequence comprising at least four bases of a target nucleic acid comprising:
(a) preparing one or more reaction mixtures containing the target nucleic acid and four or more different, overlapping primers, each primer being complementary to a portion of the target nucleic acid such that the primers each have a 3' end that hybridizes immediately 3' of a different nucleotide position of the contiguous sequence to be determined, wherein each reaction contains all of said primers and is under conditions where the primers anneal to the target nucleic acid;
(b) extending the four or more primers from (a) with a polymerase in the presence of four or more different dideoxynucleotides, each type of dideoxynucleotide having a different label;
(c) immobilizing said primers to a solid support; and
(d) detecting the label of the dideoxynucleotide incorporated into each primer and utilizing this information to determine said contiguous sequence of at least four bases of the target nucleic acid;
wherein the primers are immobilized to the solid support via a covalent attachment.

19. A method for determining a contiguous sequence comprising at least four bases of a target nucleic acid comprising:
(a) preparing one or more reaction mixtures containing the target nucleic acid and four or more different, overlapping primers, each primer being complementary to a portion of the target nucleic acid such that the primers each have a 3' end that hybridizes immediately 3' of a different nucleotide position of the contiguous sequence to be determined, wherein each reaction contains all of said primers and is under conditions where the primers anneal to the target nucleic acid;
(b) extending the four or more primers from (a) with a polymerase in the presence of four or more different dideoxynucleotides, each type of dideoxynucleotide having a different label;
(c) immobilizing said primers to a solid support; and
(d) detecting the label of the dideoxynucleotide incorporated into each primer and utilizing this information to determine said contiguous sequence of at least four bases of the target nucleic acid;
wherein the solid support is a labeled microsphere.

20. The method of claim 19, wherein the microspheres and labeled dideoxynucleotide are detected by flow cytometry.

21. The method of claim 17, wherein the solid support is a two-dimensional array and the immobilized primers are positionally defined on the array.

* * * * *